United States Patent [19]

Noguchi et al.

[11] Patent Number: 5,637,081

[45] Date of Patent: Jun. 10, 1997

[54] ANTICOAGULANT COMPOSITION FOR USE IN BLOOD DIALYSIS CIRCUIT

[75] Inventors: Yasuhisa Noguchi, Ibaraki-ken; Toshio Kasama, Tokyo, both of Japan

[73] Assignee: NOF Corporation, Tokyo, Japan

[21] Appl. No.: 460,983

[22] Filed: Jun. 5, 1995

Related U.S. Application Data

[62] Division of Ser. No. 167,221, Dec. 14, 1993, Pat. No. 5,421,815.

[51] Int. Cl.$^6$ .................................................. A61M 37/00
[52] U.S. Cl. ............................ 604/4; 524/313; 424/44
[58] Field of Search .......................... 427/2.13; 514/56; 530/393; 524/313; 604/4–6; 210/644–648; 422/44–48; 568/326

[56] References Cited

U.S. PATENT DOCUMENTS

| | | | |
|---|---|---|---|
| 3,677,710 | 7/1972 | Hirsch | 422/44 |
| 3,849,071 | 11/1974 | Kayser | 422/45 |
| 4,643,715 | 2/1987 | Isono et al. | 604/6 |
| 5,144,081 | 9/1992 | Heywang et al. | 568/326 |
| 5,167,921 | 12/1992 | Gordon | 422/46 |
| 5,178,763 | 1/1993 | Delaunay | 210/644 |

*Primary Examiner*—Robert A. Clarke
*Attorney, Agent, or Firm*—Darby & Darby

[57] ABSTRACT

An anticoagulant composition for a blood dialysis circuit contains a fatty acid derivative in liquid form at ambient temperature, and an antioxidant. The antioxidant is contained in an amount of 0.0001 to 5.0 parts by weight relative to 100 parts by weight of the fatty acid derivative. An air trap chamber device for a blood dialysis circuit contains a vessel for storing blood dialysed by a dialysis unit, an inlet tube for introducing the blood treated with dialysis into a liquid in the vessel selected from the group consisting of a layer of the aforementioned anticoagulant composition, and the blood, a measurement unit for measuring the pressure of air in the vessel lying above the layer of the anticoagulant composition, an adjustment unit for adjusting the pressure of the air and an outlet tube for conducting the blood treated with dialysis out of the vessel. A method for blood dialysis involves passing blood taken out of a mammal through the aforementioned vessel in which the blood and air are not in contact with each other, and returning the blood into the mammal.

3 Claims, 1 Drawing Sheet ature, and the blood, measurement means for mea-
ANTICOAGULANT COMPOSITION FOR USE IN BLOOD DIALYSIS CIRCUIT This is a division of application Ser. No. 08/167,221, filed Dec. 14, 1993, and issued on Jun. 6, 1995 as U.S. Pat. No. 5,421,815.

BACKGROUND OF THE INVENTION

This invention relates to an anticoagulant composition for use in a blood dialysis circuit, an air trap chamber device for the blood dialysis circuit and a method for blood dialysis in order to suppress blood coagulation and oxidation produced during blood dialysis due to contact of the blood with air.

In a venous air trap chamber, in which the pressure in the blood dialysis circuit is measured and the foreign matter, coagulated blood and air mixed into an adjustment circuit are removed, the blood is directly contacted with air. Since the blood is caused to flow at an increased rate into the air trap chamber, the blood surface is contacted with air so that the air is entrained into the blood to promote mixing and dissolution of the air into the blood frequently, resulting in the blood coagulation or activation and oxidation of the blood coagulating system. It is well known that the contact of blood with air tends to coagulate the blood. Besides, blood coagulation is promoted by the shear stress due to the blood stream. Besides, if air is contacted with the blood, the blood tends to be oxidized, that is the membrane of platelet, erythrocyte, leucocyte and lipoprotein tends to be oxidized. Oxidation is promoted by the presence of higher unsaturated fatty acids present in these membranes. Radicals from peroxide lipid produced by the oxidation leads to lesion in the endothelium of the blood vessel and to arterial sclerosis. Meanwhile, since the presence of an air layer in the air trap chamber is indispensable for pressure adjustment in the blood dialysis circuit, it is impossible in the current status of the art to remove air from the air trap chamber.

As pharmaceuticals for suppressing the blood coagulation during dialysis, heparin, low-molecular heparin, Nafamostat mesilate and have hitherto been employed. Above all, heparin is used predominantly because low-molecular heparin is more expensive.

However, it is not possible with the above pharmaceuticals to inhibit contact of the blood with air, while the blood oxidation cannot be inhibited even if blood coagulation may be inhibited. On the other hand, if used in a small amount, heparin is only poor in its ability in suppressing blood coagulation. For this reason, it is necessary to employ a large amount of heparin for prolonged time. As a result thereof, various side-effects, such as osteoporosis, hypersensitivity and lipid dysbolism due to increase in fatty acids in the blood are produced in a well-known manner. Besides, heparin has a longer intracorporeal half-life period and hence a longer hemostatic time so that it cannot be readily employed for a patient having a tendency towards hemorrhage or a patient treated with surgical operation. Although there is proposed, in conjunction with the use of heparin, a physical method of directly placing physiological saline on the blood in the air trap chamber for preventing the air and the blood from being contacted directly with each other, the practical effect is substantially nil because the air and the blood are mixed immediately. It is reported in Artificial Organs 14 Supp 14 edited by K. Ota and T. Agishi ICAOT press Cleveland 1991 (Japanese Laid-Open Patent Publication No. 2-119870) that Kitamoto et al. succeeded in floating tricaprylin on the blood in an air trap chamber to brake the contact between air and the blood.

However, since tricaprylin is used by itself, tricaprylin tends to be oxidized under the effect of a trace amount of metals in the air or blood, as a result of which the oxidized oil is brought into contact with the blood.

With the above-described conventional methods, it is not possible to prevent blood coagulation or oxidation in the air trap chamber effectively such that blood coagulation and adverse side-effects of the pharmaceuticals occur in the blood dialysis circuit. Besides, the quantity of the peroxide lipid in the blood is increased due to direct contact with air with the result that occurrence of lesions to the circulatory system such as arterial sclerosis as a complication of the patient treated with blood dialysis tends to be increased.

SUMMARY OF THE INVENTION

It is an object of the present invention to provide an anticoagulant composition for use in a blood dialysis circuit, an air trap chamber device for the blood dialysis circuit and a method for blood dialysis, whereby it is possible to prevent contact or mixing between the blood and the air or the shear stress brought about by the blood stream a well as to inhibit blood coagulation or activation of the blood coagulation system and to decrease the quantity of the anticoagulant significantly.

It is another object of the present invention to provide an anticoagulant composition for use in a blood dialysis circuit, an air trap chamber device for the blood dialysis circuit and a method for blood dialysis, whereby it is possible to inhibit blood oxidation and to prevent generation of peroxide lipid or radicals responsible for arterial sclerosis.

The above and other objects of the present invention will become apparent from the following description.

According to the present invention, there is provided an anticoagulant composition for a blood dialysis circuit comprising a fatty acid derivative in liquid form at ambient temperature, and an antioxidant, the antioxidant being contained in an amount of 0.0001 to 5.0 parts by weight relative to 100 parts by weight of the fatty acid derivative.

According to the present invention, there is also provided an air trap chamber device for a blood dialysis circuit comprising a vessel for storing blood dialysed by a dialysis unit, an inlet tube for introducing blood treated with dialysis into a liquid in the vessel selected from the group consisting of a layer of an anticoagulant composition composed of 0.0001 to 5.0 parts by weight of an antioxidant and 100 parts by weight of a fatty acid derivative in liquid form at ambient temperature, and the blood, measurement means for measuring the pressure of air in the vessel lying above the layer of the anticoagulant composition, adjustment means for adjusting the pressure of the air and an outlet tube for conducting the blood treated with dialysis out of the vessel.

According to the present invention, there is also provided a method for blood dialysis comprising the steps of: (a) taking out blood from a body of a mammal, (b) removing toxic materials from the blood by dialysis, (c) introducing the blood treated by dialysis into a liquid in a vessel selected from the group consisting of an anticoagulant composition layer containing 0.0001 to 5.0 parts by weight of an antioxidant and 100 parts by weight of a fatty acid derivative in liquid form at ambient temperature and the blood so that the blood and air are not in contact with each other, and (d) returning the blood into the body of the mammal under measuring the air pressure in the vessel and adjusting the blood flow.

PREFERRED EMBODIMENTS OF THE INVENTION

Figure 1:
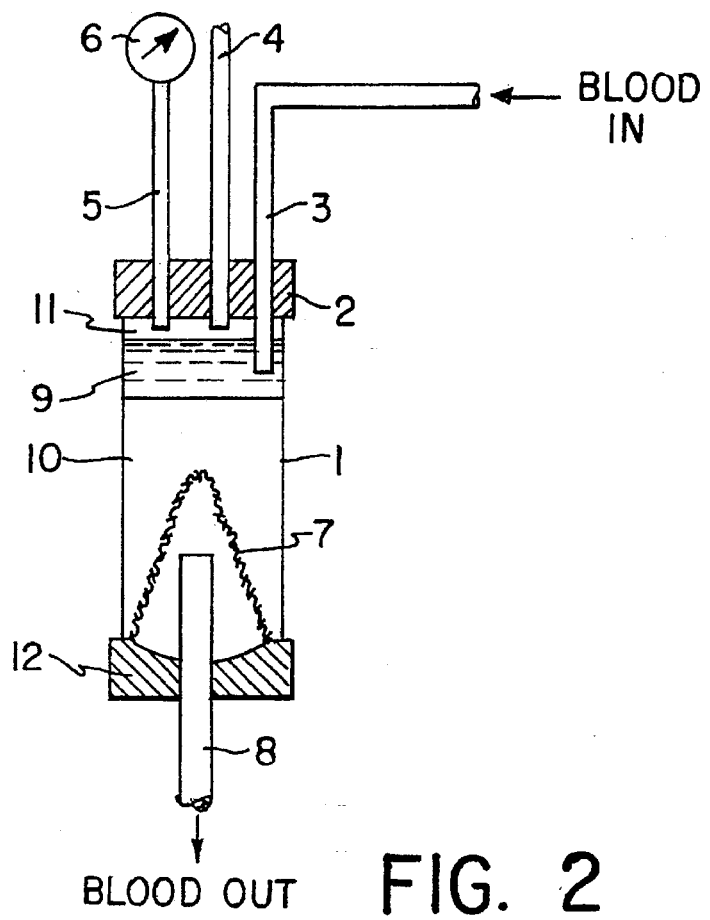
FIG. 1 is a schematic side view shown partially in section, and showing an air trap chamber for use in a blood dialysis circuit according to an embodiment of the present invention.

The present invention is explained in detail hereinbelow.

The anticoagulant composition for the blood dialysis circuit according to the present invention is characterized by containing specific amounts of a fatty acid derivative which is liquid at ambient temperature and an antioxidant. The antioxidant is effective to raise oxidation stability of the fatty acid derivative and acts to capture radicals generated in an interface between the blood and the fatty acid derivative by a small amount of air dissolved in the layer of the fatty acid derivative, while also acting to capture the radicals or the like generated by other causes, such as by a dialyzer, or generated in vivo, by dissolving these radicals in the interface with the fatty acid derivative or in the blood.

The fatty acid derivatives, which are employed in the composition of the present invention and which are liquid at ambient temperature, may be enumerated by triglycerides, which are mid chain length triglycerides, containing saturated fatty acids having 6 to 10 carbon atoms, olive oil, safflower oil, soybean oil, corn oil and esters of fatty acids. Preferred are the triglycerides having 6 to 10 carbon atoms, above all, tricaprylin containing saturated fatty acids having 8 carbon atoms. The ambient temperature herein means the temperature ranging from 1° C. to 30° C.

The antioxidants employed in the composition of the present invention may be enumerated by vitamin E, 2,6-dibutyl-p-cresol (BHT), 2-butyl-4-hydroxyanisole (BHA), epigallocatechin gallate, gallic acid, sesaminol, flavonoids, vitamin A, β-carotene and mixtures thereof. Most preferred are vitamin E and BHT. The proportion of the antioxidant is in a range of from 0.0001 to 5.0 parts by weight and preferably in a range of from 0.0001 to 1 part by weight to 100 parts by weight of the fatty acid derivative which is liquid at the ambient temperature. If the amount of the antioxidant is less than 0.0001 part by weight, the desirable antioxidant effects cannot be achieved, whereas if the amount exceeds 5.0 parts by weight, the antioxidant effect is not increased.

The composition of the present invention may be employed by mixing the fatty acid derivative with the antioxidant and injecting the resulting mixture into a space between the blood and the air contained in the air trap chamber used in the blood dialysis circuit as later explained for forming a membrane layer interrupting direct contact between the air and the blood.

The air trap chamber device according to the present invention is provided in the blood dialysis circuit employed for extracorporeal circulation of the blood for removing components in the blood, and is comprised of a membrane layer of the anticoagulant composition for use in the blood dialysis circuit between the air and the blood contained in the chamber.

According to the present invention, if the blood is introduced into the air trap chamber, the blood surface is covered by the membrane layer of the anticoagulant composition for use in the blood dialysis circuit for preventing direct contact between the blood and the air. Besides, owing to the presence of the air layer within the chamber, it becomes possible to detect the pressure within the air trap chamber as well as to effect pressure regulation.

The present invention will be explained hereinbelow by referring to an example shown in the drawings in which the air trap chamber of the present invention is applied to a blood dialysis circuit system. However, the present invention is not to be limited to this specific example.

FIG. 1 shows schematically an air trap chamber having a tubular chamber member 1. The above-mentioned anticoagulant composition for the blood dialysis circuit is injected during pre-adjustment into a space between blood 10 and air 11 in the tubular chamber member 1 for forming a membrane layer 9 of the anticoagulant composition for the blood dialysis circuit having a thickness of approximately 10 mm. The thickness of the membrane layer 9 is preferably 2 to 20 mm and most preferably on the order of 10 mm. If the thickness is less than 2 mm, separation between the blood 10 and the air 11 may become unstable. The thickness in excess of 20 mm is not desirable since it may not be effective and, besides, the spacing within the air trap chamber is decreased.

On the top of the tubular chamber member 1, there is provided a cap 2, to which there are connected a blood inlet tube 3 via which the blood passed through a blood dialyzer, not shown, is introduced, a tube 4 connected to a level adjustment line and a pressure monitoring line tube 5 connected in turn to a pressure gauge 6. The distal ends of the tube 4 and the pressure monitoring line tube 5 are placed within the air 11. If pressure fluctuations are produced within the blood circuit, the pressure within the air 11 is changed. Such pressure change may be measured by the pressure gauge 6 via the pressure monitoring line tube 5 so that the pressure in the air 11 may be adjusted via the tube 4. The distal end of the blood inlet tube 3 is placed within the membrane layer 9 to prevent the blood from being contacted with the air 11. Alternatively, the distal end of the blood inlet tube 3 may be placed within the blood 10. The lower end of the tubular chamber member 1 is provided with a cap 12 connected to a blood outlet tube 8. The blood caused to flow via the blood inlet tube 3 is passed through a filter mesh 7 so as to be freed of air and foreign matters. The blood purified in this manner is caused to flow via the blood outlet tube 8 out of the air trap chamber for the blood dialysis circuit so as to be returned to the patient.

It is noted that the air trap chamber for the blood dialysis circuit according to the present invention may be applied not only to the blood dialysis system, but also to a blood circuit for exchanging blood serum and to treatment by extracorporeal circulation of a body fluid other than blood, such as abdominal dropsy.

The anticoagulant composition for the blood dialysis circuit according to the present invention, composed of a fatty acid derivative which is liquid at ambient temperature and an antioxidant, is extremely stable and capable of inhibiting generation of peroxide lipid and radicals and suppressing blood coagulation or activation of the blood coagulating system. Besides, it is possible with the air trap chamber device for the blood dialysis circuit of the present invention to interrupt the contact between the blood and the air to prevent thrombus and blood oxidation. In this manner, an anticoagulant agent may be reduced significantly in quantity or dispensed with, while pressure measurement and adjustment in the blood dialysis circuit may be performed as conventionally.

EXAMPLES OF THE INVENTION

The present invention will be explained further with reference to Examples which are given only by way of illustration.

Example 1

35 beagles, 5 to 7 months of age, were separated into five groups, namely a control group, a heparin group, a tricaprylin group, a tricaprylin/vitamin E group, referred to hereinafter as a vitamin E group, and a tricaprylin/BHT group, referred to hereinafter as a BHT group, each consisting of seven animals. The beagles were put in stainless steel cages in a keeping chamber at a rate of one animal in each cage and kept. The keeping chamber was set to a temperature of 24°±2° C., a humidity of 55±15%, a lighting time duration of 12 hours (since 7 a.m. until 7 p.m.) and the number of times of ventilation of 15 per hour. The animals were fed with 300 g per day of solid feeds and about 1800 ml of water, with the feed and water being supplied freely by feed cups.

Figure 2:
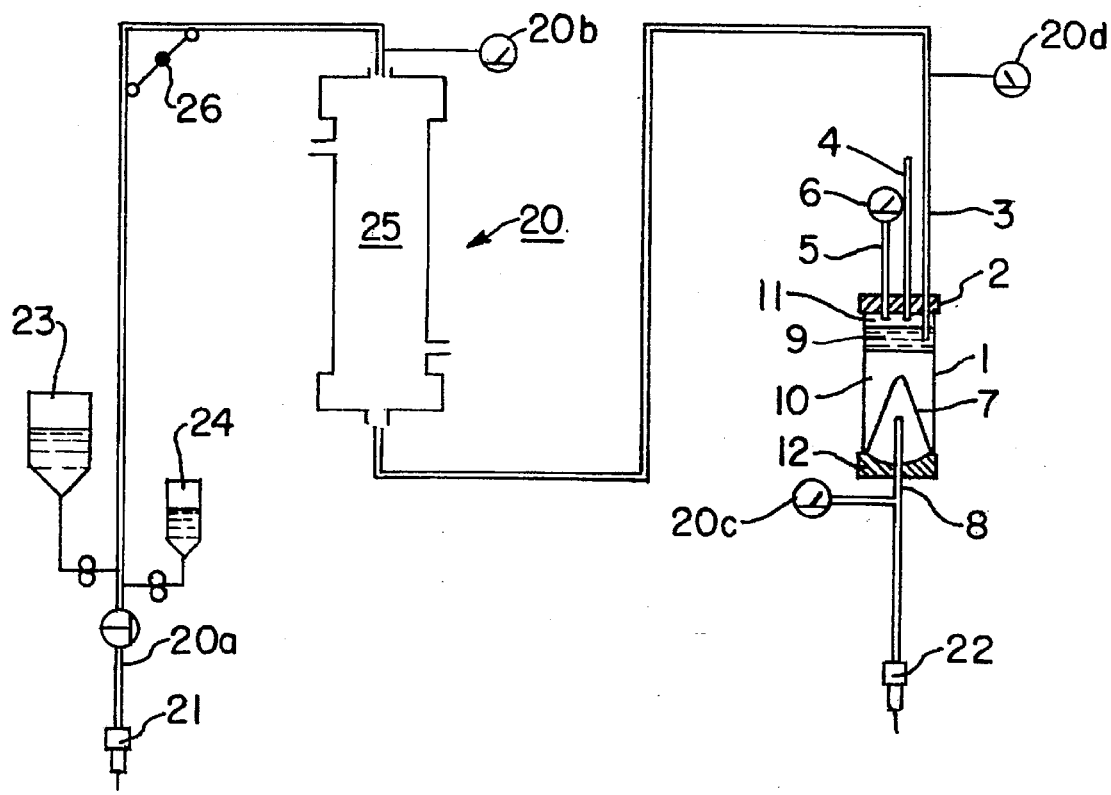
FIG. 2 is a schematic view showing a blood dialysis circuit system incorporating the air trap chamber shown in FIG. 1.

The air trap chamber shown in FIG. 1 was equipped as a vein side chamber of a blood dialysis circuit system shown in FIG. 2. The air trap chamber is the same as that shown in FIG. 1 so that the respective components of the air trap chamber are denoted by numerals which are the same as those shown in FIG. 1 and the corresponding description is omitted. The blood dialysis circuit system thus equipped with the air trap chamber was fitted on each beagle for measurement. The membrane layer 9, formed by the anticoagulant composition for the blood dialysis circuit in the vein side chamber loaded on each animal of the respective test groups was not formed for the control group. The membrane layer was formed for the heparin group by administering heparin 24 diluted with physiological saline 23 at a rate of 20 units per kg after taking out the blood via a blood-sampling cannula 21 of the blood dialysis circuit system 20 immediately after start of dialysis, 20 minutes and 40 minutes after start of the dialysis. The membrane layer was formed for the tricaprylin group by quietly adding 5 ml of tricaprylin on the blood in the vein side chamber of the blood dialysis circuit system 20 immediately before start of dialysis for forming the membrane layer 9 which was 10 mm in thickness. The membrane layer was formed for the vitamin E group by adding 1.5 mg of natural vitamin E to 5 ml of tricaprylin for forming a membrane layer 9 in the same manner as for the tricaprylin group, while the membrane layer for the BHT group was formed by adding 2.5 mg of BHT to 5 ml of tricaprylin for forming the membrane layer 9 in the same manner as for the tricaprylin group.

Method of Dialysis: For conducting dialysis, the blood-intake cannula 21 made of polyethylene and a blood-returning cannula 22 made of polyethylene were inserted into a left femoral vein and a right femoral vein of each of the beagles of the respective test groups, respectively, under anesthesia caused by intravenous administration of 30 mg/kg of Nembutal. The blood dialysis circuit system 20 was loaded on each of the beagles. The blood dialysis circuit and the dialyzer 25 were primed with sufficiently deaerated physiological saline to prevent air from being mixed into the circuit. The blood was fed by a blood flow pump 26 to the dialyzer 25. The blood level in the vein side chamber was set to the level at the blood inlet. The extracorporeal circulation was carried out for 60 minutes at the blood quantity of 150 ml/min.

Test Method:

The blood activation and coagulation time duration was measured on the blood sampled from an artery side circuit 20a in 0, 20, 40 and 60 minutes since the start of dialysis using a measurement device manufactured and sold by JAPAN MEDICAL SUPPLY CO., LTD. under the trade name of "ACTESTER". The results are shown in Table 1.

TABLE 1

Extension of Activated and Coagulation Time Duration (Before Start of Extracorporeal Circulation) (%)

| Sample Time (Min) | Control Group | Heparin Group | Tricaprylin Group | Vitamin E Group | BHT Group |
| --- | --- | --- | --- | --- | --- |
| 0 | 103 ± 1 | 106 ± 2 | 106 ± 2 | 105 ± 2 | 104 ± 2 |
| 20 | 102 ± 3 | 135 ± 6 | 103 ± 2 | 104 ± 3 | 103 ± 3 |
| 40 | 102 ± 2 | 145 ± 9 | 105 ± 3 | 105 ± 3 | 104 ± 2 |
| 60 | 103 ± 2 | 142 ± 5 | 106 ± 3 | 103 ± 2 | 105 ± 2 |

It is seen from the results of Table 1 that the tricaprylin group, the vitamin E group and the BHT group did not change similarly to the control group in that the blood coagulation time was not extended and the tendency for the hemorrhage was not displayed for these groups as compared to the heparin group.

In the dialyzer 25, the circuit was flushed with physiological saline in 20, 40 and 60 minutes after the start of dialysis and the degree of blood coagulation in the dialyzer 25 was checked by visual observation and photographing. The degree of blood coagulation was measured on the basis of the proportion of the coagulated area. The results are shown in Table 2.

TABLE 2

Degree of Blood Coagulation in Dialyzer

| Sample Time (Min) | Control Group | Heparin Group | Tricaprylin Group | Vitamin E Group | BHT Group |
| --- | --- | --- | --- | --- | --- |
| 20 | 11 ± 1 | 4 ± 1 | 6 ± 1 | 6 ± 2 | 7 ± 2 |
| 40 | 43 ± 4 | 18 ± 4 | 23 ± 3 | 20 ± 2 | 23 ± 3 |
| 60 | 70 ± 3 | 36 ± 6 | 44 ± 6 | 41 ± 5 | 40 ± 5 |

It is seen from the results shown in Table 2 that the tricaprylin group, the vitamin E group and the BHT group exhibited the ability of suppressing blood coagulation comparable to that of the heparin group in the dialyzer 25 and a blood coagulation degree lower than that in the control group.

The blood coagulated after 60 minutes was sampled via the blood inlet 3 and the mesh 7 and measured as the total protein mass by the Lowry method. The results are shown in Table 3.

TABLE 3

Amount of Blood Coagulated after 60 Minutes in Chamber (mg) (As Total Protein)

| Sample Protein in Chamber | Control Group | Heparin Group | Tri-caprylin Group | Vitamin E Group | BHT Group |
| --- | --- | --- | --- | --- | --- |
| Blood Inlet | 21.5 ± 4.1 | 2.2 ± 1.0 | 0.0 ± 0.0 | 0.0 ± 0.0 | 0.0 ± 0.0 |
| Mesh | 28.4 ± 6.8 | 6.6 ± 2.5 | 9.0 ± 4.0 | 8.3 ± 3.7 | 8.8 ± 3.9 |

It is seen from the results of Table 3 that the tricaprylin group, the vitamin E group and the BHT group displayed no blood coagulation at the blood inlet 3 in the chamber and suppressed blood coagulation at the mesh 7 as compared to the control group.

The pressure in the circuit was monitored using a pressure gauge 20b on the front side of the dialyzer, the pressure gauge 6 at the vein side chamber and a pressure gauge 20d at the rear side of the dialyzer. The measured values of the pressure are shown in Table 4.

TABLE 4

Internal Pressure in Dialyzer and Chamber (mmHg)

| Sample Time (Min) | Location | Control Group | Heparin Group | Tricaprylin Group | Vitamin E Group | BHT Group |
|---|---|---|---|---|---|---|
| 0–5 | Dialyzer | 156 ± 8 | 144 ± 5 | 150 ± 2 | 148 ± 4 | 153 ± 7 |
|  | Chamber | 36 ± 4 | 27 ± 1 | 38 ± 7 | 35 ± 7 | 35 ± 4 |
| 20 | Dialyzer | 202 ± 11 | 177 ± 4 | 188 ± 8 | 182 ± 6 | 183 ± 10 |
|  | Chamber | 63 ± 8 | 38 ± 2 | 49 ± 7 | 44 ± 5 | 41 ± 6 |
| 40 | Dialyzer | 254 ± 20 | 205 ± 8 | 222 ± 10 | 211 ± 12 | 214 ± 9 |
|  | Chamber | 102 ± 14 | 51 ± 7 | 63 ± 9 | 60 ± 11 | 59 ± 7 |
| 60 | Dialyzer | 306 ± 17 | 244 ± 24 | 237 ± 11 | 233 ± 9 | 240 ± 12 |
|  | Chamber | 112 ± 14 | 70 ± 11 | 63 ± 9 | 63 ± 7 | 66 ± 6 |

It is seen from the results of Table 4 that the tricaprylin group, the vitamin E group and the BHT group displayed less internal pressure increase in the dialyzer 25 or in the air trap chamber than that with the control group, so that the tricaprylin group, the vitamin E group and the BHT group suppressed blood coagulation in the blood dialysis circuit similarly to the heparin group.

The peroxide value of each of the tricaprylin group, the vitamin E group and the BHT group was measured before and after dialysis by an iodometric method for inspection of stability between the two states. The results are shown in Table 5.

TABLE 5

| Peroxide Value | | | | | |
|---|---|---|---|---|---|
| Tricaprylin Group | | Vitamin E Group | | BHT Group | |
| Before Dialysis | After Dialysis | Before Dialysis | After Dialysis | Before Dialysis | After Dialysis |
| 0.32 ± 0.13 | 2.16 ± 0.28 | 0.32 ± 0.11 | 0.36 ± 0.10 | 0.32 ± 0.10 | 0.35 ± 0.12 |

It is seen from the results of Table 5 that the vitamin E group and the BHT group showed no increase in the peroxide value even after end of dialysis continuing for 60 minutes and thus remained more stable than the tricaprylin group.

Immediately before dialysis and after 60 minutes after the end of dialysis, blood was sampled from an artery side circuit 20a, and serum lipid was extracted from the blood sample using a 1/2 mixed solvent of chloroform/methanol. The peroxide lipid of the blood serum was measured by chemical light emitting liquid chromatography with phosphatidyl choline hydroperoxide in the serum lipid as control. The results are shown in Table 6.

TABLE 6

| Phosphatidyl Choline Hydroperoxide in Serum Lipid (nM) | | | | | |
|---|---|---|---|---|---|
| Sample Time (Min) | Control Group | Heparin Group | Tricaprylin Group | Vitamin E Group | BHT Group |
| 0 | 216 ± 32 | 203 ± 28 | 219 ± 33 | 210 ± 27 | 208 ± 2 |
| 60 | 321 ± 37 | 318 ± 35 | 245 ± 27 | 218 ± 31 | 220 ± 2 |

It is seen from the results of Table 6 that phosphatidyl choline hydroperoxide in the serum lipid in each of the control group and the heparin group exhibited marked increase in 60 minutes since the start of dialysis, whereas that in the tricaprylin group showed only a minor increase and that in each of the vitamin E group and the BHT group was hardly increased. That is, with the vitamin E group and the BHT group, the increase in the peroxide lipid in the serum was evidently suppressed during dialysis.

It may be confirmed from the results of the Tables 1 to 6 that, with the vitamin E group and the BHT group, it is possible to inhibit coagulation and oxidation of the blood due to contact between the blood and the air in the chamber during the blood dialysis as well as to inhibit an increase in the peroxide value in the membrane layer 9 composed of the anticoagulant composition for the blood dialysis circuit and to inhibit generation of peroxides in the serum lipid.

Although the present invention has been described with reference to the preferred examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A composition for a blood dialysis circuit consisting essentially of a triglyceride of a saturated fatty acid having 6 to 10 carbon atoms in liquid form at ambient temperature, and an antioxidant, said antioxidant being contained in an amount of 0.0001 to 5.0 parts by weight relative to 100 parts by weight of said triglyceride; wherein said composition acts as an anticoagulant.

2. The composition as claimed in claim 1 wherein said triglyceride of saturated fatty acid is tricaprylin containing a saturated fatty acid having 8 carbon atoms.

3. The composition as claimed in claim 1 wherein said antioxidant is selected from the group consisting of vitamin E, 2,6-dibutyl-p-cresol, 2-butyl-4-hydroxyanisole, epigallo-catechin gallate, gallic acid, sesaminol, flavonoids, vitamin A, β-carotene and mixtures thereof.

* * * * *